(12) United States Patent
Uehara (10) Patent No.: US 10,729,400 B2
(45) Date of Patent: Aug. 4, 2020

(54) RADIOGRAPHY SUPPORTER AND RADIOGRAPHY SUPPORT METHOD

(71) Applicant: Konica Minolta Inc., Chiyoda-ku Tokyo (JP)

(72) Inventor: Takahisa Uehara, Yokohama (JP)

(73) Assignee: KONICA MINOLTA, INC., Chiyoda-ku Tokyo (JP)

( * ) Notice: Subject to any disclaimer, the term of this patent is extended or adjusted under 35 U.S.C. 154(b) by 0 days.

(21) Appl. No.: 16/127,459

(22) Filed: Sep. 11, 2018

(65) Prior Publication Data

US 2019/0076109 A1    Mar. 14, 2019

(30) Foreign Application Priority Data

Sep. 12, 2017   (JP) .................................. 2017-174882

(51) Int. Cl.
    *A61B 6/00*      (2006.01)
    *G01T 1/161*     (2006.01)

(52) U.S. Cl.
    CPC .............. *A61B 6/545* (2013.01); *A61B 6/56* (2013.01); *G01T 1/161* (2013.01); *A61B 6/465* (2013.01); *A61B 6/469* (2013.01); *A61B 6/548* (2013.01)

(58) Field of Classification Search
    CPC ....................................... A61B 6/545
    See application file for complete search history.

(56) References Cited

U.S. PATENT DOCUMENTS

2013/0336456 A1* 12/2013 Tanaka .................... H05G 1/30
                                                      378/91

FOREIGN PATENT DOCUMENTS

JP       2002200062 A    7/2002
JP       2014000131 A    1/2014

* cited by examiner

*Primary Examiner* — Dani Fox
(74) *Attorney, Agent, or Firm* — Cantor Colburn LLP (57) ABSTRACT

A radiography supporter supports a radiography system including a radiation generator and a radiography apparatus in taking radiographic images, and the radiography supporter includes a hardware processor that: acquires an examination order; transmits corresponding radiation irradiation conditions to the radiation generator, for each examination order; and restricts transmission of irradiation conditions corresponding to a second examination order to be executed after a specific first examination order in a case where a plurality of the examination orders has been acquired for a same examination object, and the irradiation conditions corresponding to the first examination order have been changed.

8 Claims, 5 Drawing Sheets

ID: 11111　NAME OF PATIENT: OO TARO　DATE OF BIRTH: yyyy/mm/dd　SEX: MALE

EXAMINATION ORDER 1 (UPRIGHT AP CHEST)

EXAMINATION ORDER 2 (UPRIGHT PA CHEST)

READY FOR RADIOGRAPHY

[RADIOGRAPHY CONDITIONS]
TUBE VOLTAGE: 90kV
TUBE CURRENT: 160mA
IRRADIATION TIME: 63ms

PI — ID: 11111  NAME OF PATIENT: OO TARO  DATE OF BIRTH: yyyy/mm/dd  SEX: MALE

B11 — EXAMINATION ORDER 1 (UPRIGHT AP CHEST)
B12 — EXAMINATION ORDER 2 (UPRIGHT AP ABDOMEN)

90kV
160mA
63ms

A

READY FOR RADIOGRAPHY

NOT IN LINKAGE.
DO YOU TRANSMIT IRRADIATION
CONDITIONS?
(Y/N)

MD

D

RADIOGRAPHY SUPPORTER AND RADIOGRAPHY SUPPORT METHOD

CROSS REFERENCE TO RELATED APPLICATIONS

The present application claims priority under 35 U.S.C. § 119 to Japanese patent application No. 2017-174882, filed on Sep. 12, 2017, and the entire disclosure of which is incorporated herein by reference.

BACKGROUND

Technological Field

The present invention relates to a radiography supporter and a radiography support method for supporting a radiography system in taking radiographic images.

Description of the Related Art

Conventionally, diagnostic imaging using an X-ray photography system has been performed in the medical field. In recent years, along with development of a flat panel detector (FPD) that generates an X-ray image based on incident X-rays, a diagnosis method using roentgenkymography is also being established. In roentgenkymography, it is possible to obtain not only morphological information of respiratory organs and circulatory organs but also dynamic information from a change in pixel values (concentration) of an X-ray image. For example, it is possible to perform chest dynamic diagnosis related to a pulmonary ventilation function, pulmonary blood flow, and others.

In general, an X-ray photography system includes an X-ray generator and an X-ray photography apparatus. The X-ray generator generates and emits X-rays toward an examination object. The X-ray photography apparatus takes an X-ray image based on a dose of incident X-rays having passed through the examination object.

The X-ray generator includes an X-ray tube assembly, a high-voltage generator, an X-ray generation controller, an X-ray generation console, an irradiation switch, and the like. The X-ray tube assembly emits X-rays toward an examination object. The high-voltage generator applies voltage to the X-ray tube assembly. The X-ray generation controller controls operation of the X-ray tube assembly and the high-voltage generator. The X-ray generation console is used for inputting and confirming irradiation conditions and the like. The irradiation switch is used for providing an instruction for X-ray irradiation.

The X-ray photography apparatus includes an FPD, a radiography control apparatus, and a radiography console. The FPD detects X-rays having passed through an examination object, converts the X-rays into image data, and outputs the image data. Along with controlling operation of the FPD, the radiography control apparatus performs predetermined processing (for example, image processing and display control processing) on the obtained X-ray image data. The radiography console is used for inputting and confirming radiography conditions and the like. The X-ray image taken is displayed on the radiography console.

In the X-ray photography system, irradiation conditions are set in advance according to an examination order in the case where radiography is performed. In general, irradiation conditions are set through the X-ray generation console. Recently, irradiation conditions set in advance according to radiography details of an examination order are automatically set in the X-ray generator with cooperation between the X-ray generator and the X-ray photography apparatus when an instruction for executing the examination order is provided in the X-ray photography apparatus (for example, JP 2002-200062 A and JP 2014-000131 A).

Incidentally, irradiation conditions set in advance according to radiography details of an examination order are suitable for the case of examining an examination object with standard proportions. Therefore, even if radiography conditions are automatically set in the X-ray generator, a user (radiation technologist) needs to make fine adjustments to the irradiation conditions according to the body type and the like of an examination object in the case where the examination object is overweight or underweight.

In a conventional general X-ray photography system, upon an instruction for executing an examination order, fine-tuned radiography conditions are reset, and radiography conditions need to be set again accordingly even in the case where there exists a plurality of examination orders for the same examination object, and it is clear that radiography conditions need to be fine-tuned. Meanwhile, JP 2014-000131 A discloses the following technique. In the case where there exists a plurality of examination orders for the same examination object, and radiography details (for example, areas to be X-rayed and radiographing directions) of consecutive examination orders are the same, radiography conditions fine-tuned in taking X-rays in the previous examination are prioritized, and even if an instruction for executing a subsequent radiography examination order is provided, restrictions are imposed so as to prevent radiography conditions from being set. As a result, an operation burden on a user is reduced.

However, although the technique disclosed in JP 2014-000131 A is effective when radiography details of consecutive examination orders are the same, the order in which examination orders are executed is restricted. For example, even if there exists a plurality of examination orders with the same radiography details for the same examination object, fine-tuned radiography conditions are reset unless these examination orders are consecutively executed.

Generally, in the case where there exists a plurality of examination orders for the same examination object, it often happens that areas to be X-rayed are the same, but X-ray irradiation directions (front/back/side) are different. Accordingly, it is rare that radiography details are quite the same or similar. Therefore, it cannot be said that the technique disclosed in JP 2014-000131 A significantly reduces an operation burden on a user. Meanwhile, whether to set irradiation conditions is determined for each examination order. This surely increases a processing burden on a computer. As described above, it cannot be said that the technique disclosed in JP 2014-000131 A efficiently reduces an operation burden on a user.

SUMMARY

An object of the present invention is to provide a radiography supporter and a radiography support method that can efficiently reduce an operation burden on a user in setting irradiation conditions of a radiation generator.

To achieve the abovementioned object, according to an aspect of the present invention, there is provided a radiography supporter that supports a radiography system including a radiation generator and a radiography apparatus in taking radiographic images, and the radiography supporter reflecting one aspect of the present invention comprises a hardware processor that:

acquires an examination order;

transmits corresponding radiation irradiation conditions to the radiation generator, for each examination order; and restricts transmission of irradiation conditions corresponding to a second examination order to be executed after a specific first examination order in a case where a plurality of the examination orders has been acquired for a same examination object, and the irradiation conditions corresponding to the first examination order have been changed.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described in detail with reference to the drawings. However, the scope of the invention is not limited to the disclosed embodiments.

Figure 1:
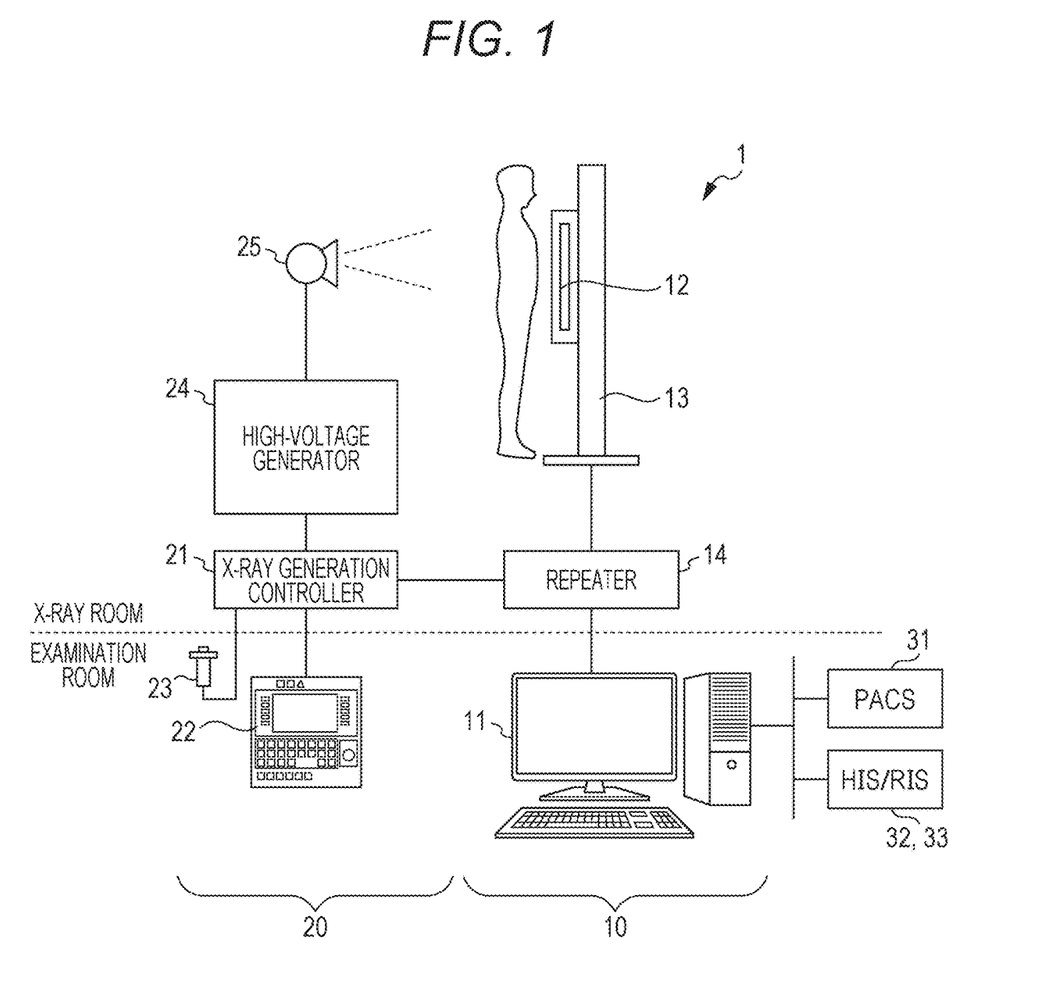
FIG. 1 is a diagram showing an X-ray photography system to which a radiography supporter according to one embodiment of the present invention has been applied.

FIG. 1 is a diagram showing an X-ray photography system 1 to which a radiography supporter according to one embodiment of the present invention has been applied. In the X-ray photography system 1, the radiography supporter according to the present invention has been applied to a radiography control apparatus 11. The X-ray photography system 1 is an integrated radiographing system in which an X-ray generator 20 and an X-ray photography apparatus 10 exchange signals and the like with each other, and take X-rays in cooperation with each other.

As shown in FIG. 1, the X-ray photography system 1 includes the X-ray photography apparatus 10 and the X-ray generator 20. The X-ray photography system 1 is connected, via a communication network, to a picture archiving and communication system (PACS) 31, a hospital information system (HIS) 32, and a radiology information system (RIS) 33. In the communication network including the X-ray photography system 1, the PACS 31, the HIS 32, and the RIS 33, information is transmitted and received in conformity with, for example, the Digital Imaging and Communications in Medicine (DICOM) standard.

The X-ray photography apparatus 10 includes the radiography control apparatus 11, a flat panel detector (FPD) 12, a radiography platform 13, a repeater 14, and the like. For example, the X-ray photography apparatus 10 visualizes X-rays that have passed through an area to be X-rayed, such as the chest and the abdomen, and takes an X-ray image showing the state inside the body.

The FPD 12 is an imaging device that detects X-rays emitted from an X-ray tube assembly 25 and having passed through an examination object, and outputs X-ray image data. For example, the FPD 12 is mounted on the radiography platform 13, and is connected to the radiography control apparatus 11 via the radiography platform 13 and the repeater 14 in a communicable manner through wire communication. The FPD 12 may be connected to the radiography control apparatus 11 through wireless communication. When the FPD 12 has a wireless communication function, the FPD 12 can be used while being placed on a bed on which an examination object lies supine, or held by the examination object him/herself, instead of being mounted on the dedicated radiography platform 13.

The FPD 12 includes, for example, a scintillator that converts incident X-rays into light, photo diodes (PDs) arranged in a matrix corresponding to pixels, and thin film transistor (TFT) switches arranged in a manner corresponding to each PD (none of them is shown in the drawings). Incident X-rays are converted into light by the scintillator, enter the PDs, and are accumulated as electric charge for each pixel. The electric charge accumulated in the PDs flows out through the TFT switches and signal lines, and is output as X-ray image data to the radiography control apparatus 11 after being amplified and subjected to analog-digital (A/D) conversion. It should be noted that the FPD 12 may be of the above-described indirect conversion type, or may be of a direct conversion type which directly converts X-rays into electric signals.

The radiography platform 13 holds the FPD 12 in a detachable manner such that the X-ray incidence plane of the FPD 12 faces the X-ray tube assembly 25. FIG. 1 shows an upright radiography platform for taking X-rays of an examination object in the upright position, as an example of the radiography platform 13. The radiography platform 13 may be a decubitus radiography platform for taking X-rays of an examination object in the decubitus position. For example, the radiography platform 13 is connected to the radiography control apparatus 11 via the repeater 14 in a communicable manner through wire communication.

The radiography control apparatus 11 controls the radiography system 1 in cooperation with an X-ray generation controller 21. For example, the radiography control apparatus 11 transmits detection conditions to the FPD 12 to set the detection conditions. Detection conditions include the size of an image to be taken, a frame rate (in the case of roentgenkymography), and information on signal processing to be executed in the FPD 12 (for example, the gain of an amplifier). Along with controlling each operation of the FPD 12, the radiography control apparatus 11 acquires X-ray image data from the FPD 12, performs predetermined image processing on the X-ray image data, and causes a display 113 (see FIG. 2) to display the processed X-ray image data. Details of the radiography control apparatus 11 will be described below.

It should be noted that the radiography control apparatus 11 may constitute a part of the X-ray generator 20. For example, the radiography control apparatus 11 can have a function as an X-ray generation console 22 of the X-ray generator 20 (so-called integrated X-ray photography system).

The X-ray generator 20 includes the X-ray generation controller 21, the X-ray generation console 22, an irradiation switch 23, a high-voltage generator 24, and the X-ray tube assembly 25.

The X-ray tube assembly 25 is disposed at a position opposed to the FPD 12 with an examination object interposed therebetween. As the high-voltage generator 24 applies high voltage to the X-ray tube assembly 25, the X-ray tube assembly 25 generates and emits X-rays toward the examination object. The X-ray tube assembly 25 includes an X-ray movable diaphragm for adjusting the irradiation field of X-rays.

The X-ray generation console 22 and the irradiation switch 23 are connected to the X-ray generation controller 21 via a signal cable. The X-ray generation console 22 is a console for, for example, inputting irradiation conditions. The irradiation switch 23 is a switch to be used for providing an instruction to perform X-ray irradiation, and includes, for example, a two-stage automatic return push button switch. When a first-stage depression operation is performed on the irradiation switch 23, a warm-up start signal for starting a warm-up of the X-ray tube assembly 25 is transmitted to the X-ray generation controller 21. When a second-stage depression operation is performed, an irradiation start signal for causing the X-ray tube assembly 25 to start X-ray irradiation is transmitted to the X-ray generation controller 21.

The X-ray generation controller 21 controls operation of the high-voltage generator 24 and the X-ray tube assembly 25, based on irradiation conditions provided from the X-ray generation console 22 and the control signals (warm-up start signal and irradiation start signal) provided from the irradiation switch 23. For example, irradiation conditions include a plurality of parameters such as tube voltage, tube current, exposure time, an exposure dose, a setting mode, focus size, a phototimer, collimator size, a filter type, and posture in radiography (upright/decubitus).

Irradiation conditions can be set through the X-ray generation console 22, or can be set by use of the radiography control apparatus 11. In the case where the X-ray photography apparatus 10 and the X-ray generator 20 operate in cooperation with each other, when an instruction for executing an examination order is provided in the radiography control apparatus 11, irradiation conditions set in advance corresponding to the examination order are automatically transmitted to the X-ray generation controller 21, and are set therein. In this case, a user can make fine adjustments to the irradiation conditions through the X-ray generation console 22.

Figure 2:
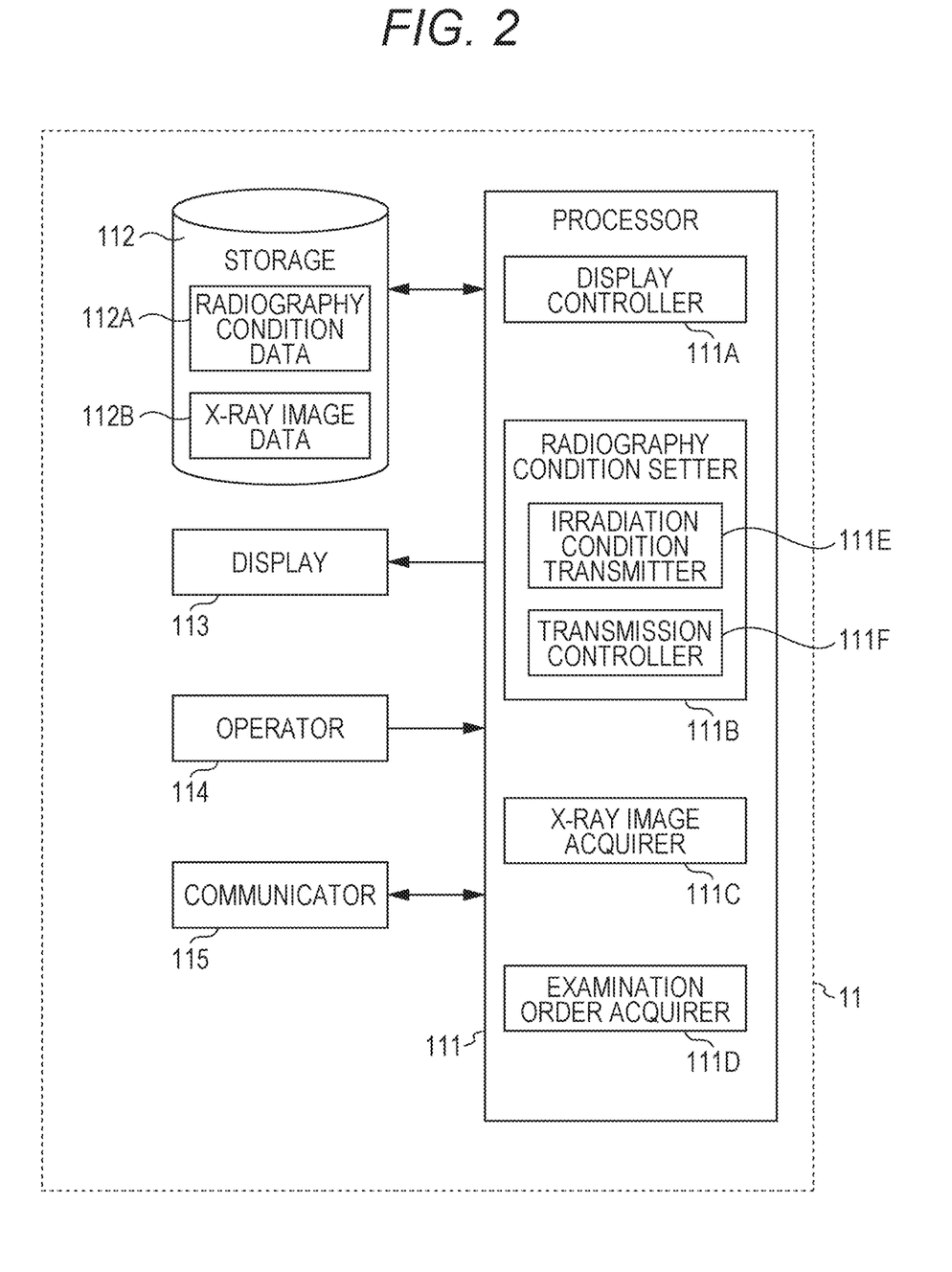
FIG. 2 is a diagram showing a configuration of a radiography control apparatus.

FIG. 2 is a diagram showing a configuration of the radiography control apparatus 11. As shown in FIG. 2, the radiography control apparatus 11 includes a processor 111, a storage 112, the display 113, an operator 114, a communicator 115, and the like.

The processor 111 includes a central processing unit (CPU) as an arithmetic/control unit, a read only memory (ROM) and a random access memory (RAM) as main storage, and the like (none of them is shown in the drawings). The ROM stores basic programs and basic setting data. The CPU centrally controls operation of the FPD 12 and the like by reading a program corresponding to processing details from the ROM or the storage 112, decompressing the program in the RAM, and executing the decompressed program. In the present embodiment, the processor 111 executes irradiation condition setting processing in radiography to efficiently reduce an operation burden on a user in setting irradiation conditions of the X-ray generator 20.

For example, the storage 112 is an auxiliary storage device such as a hard disk drive (HDD) and a solid state drive (SSD). The storage 112 may be a disk drive that reads and writes information by driving an optical disk such as a compact disc (CD) and a digital versatile disc (DVD), or a magneto-optical disk (MO). Furthermore, as another example, the storage 112 may be a memory card such as a USB flash drive and a secure digital (SD) card.

The storage 112 stores various programs to be executed in the processor 111, parameters necessary for executing the programs, and data such as processing results. The storage 112 stores, for example, radiography condition data 112A and X-ray image data 112B. The radiography condition data 112A include data of irradiation conditions in the X-ray generator 20 and data of detection conditions in the FPD 12.

Radiography conditions are associated with, for example, radiography details (an area to be X-rayed, a radiographing direction, the somatotype of an examination object, and the like) included in an examination order. When an examination order is selected, and no radiography conditions are set for the examination order (for example, at the time of an initial examination), radiography conditions associated with radiography details are read out. It should be noted that an initial examination refers to an initial examination to be performed with the same radiography details for the same examination object.

The display 113 includes, for example, a flat panel display such as a liquid crystal display and an organic electroluminescence (EL) display. Based on a display control signal from the processor 111, the display 113 displays details of an examination order and an X-ray image taken. An examination order includes patient information (for example, patient ID, name of patient, date of birth, and sex) of a patient as an examination object, information on posture in radiography (for example, posture (upright/decubitus) and irradiation direction (back/front/side)), information on an area to be X-rayed (for example, chest), examination items (pulmonary ventilation function, pulmonary blood flow, and the like), and an examination history of the examination object (radiography conditions of the previous examination, and the like).

The operator 114 includes a keyboard having cursor keys, numeric input keys, various function keys, and the like, and a pointing device such as a mouse. The operator 114 receives an operation signal input by a key operation or a mouse operation, and outputs the operation signal to the processor 111. A user can input, for example, radiography conditions through the operator 114.

It should be noted that the display 113 and the operator 114 may be integrally configured like, for example, a flat panel display with a touch panel.

For example, the communicator 115 is a communication interface such as a network interface card (NIC), a modulator-demodulator (MODEM), and a universal serial bus (USB). Via the communicator 115, the processor 111 transmits and receives various kinds of information to and from a device connected to a network, such as a wired/wireless LAN, in conformity with the DICOM standard. A communication interface for short-range wireless communication such as Near Field Communication (NFC) and Bluetooth (registered trademark) can also be applied to the communicator 115.

The processor 111 functions as a display controller 111A, a radiography condition setter 111B, an X-ray image acquirer 111C, and an examination order acquirer 111D, by executing a radiography program. The radiography condition setter 111B includes an irradiation condition transmitter 111E and a transmission controller 111F. These functions will be described in detail according to a flowchart shown in FIG. 3. The radiography program is stored in, for example, the ROM of the processor 111.

When radiography is performed by the X-ray photography system 1, an examination order is registered in the radiography control apparatus 11 (examination order acquirer 111D). The registered examination order is displayed on the display 113 of the radiography control apparatus 11 (see FIG. 4). An examination order may be input from an external system such as the HIS 32 and the RIS 33, or may be manually input by a user through the operator 114. Here, it is assumed that an examination order is input from an external system such as the HIS 32 and the RIS 33.

When an instruction for executing the registered examination order is provided, radiography conditions included in the examination order are transmitted to the X-ray generation controller 21 and the FPD 12, and are set therein (radiography condition setter 111B). It should be noted that in the initial examination, radiography conditions corresponding to radiography details included in the examination order are read from the storage 112, and are set. A user can make fine adjustments to irradiation conditions by changing the settings of the irradiation conditions through the X-ray generation console 22. When the settings of the irradiation conditions are changed, a signal indicating a change in settings is transmitted from the X-ray generation controller 21 to the radiography control apparatus 11.

When a user performs the first-stage depression operation on the irradiation switch 23, a warm-up (heating of a filament, and others) of the X-ray tube assembly 25 is started. Along with this, a ready signal (irradiation preparation start signal) indicating that a warm-up has been started is transmitted from the X-ray generation controller 21 to the radiography control apparatus 11. Upon receiving the ready signal, the radiography control apparatus 11 instructs the FPD 12 to prepare for radiography (to initialize).

Upon completion of the warm-up of the X-ray tube assembly 25, a start signal (irradiation preparation completion signal) indicating that the warm-up has been completed is transmitted from the X-ray generation controller 21 to the radiography control apparatus 11. Furthermore, an OK signal (radiography preparation completion signal) indicating that preparation for radiography has been completed is transmitted from the FPD 12 to the radiography control apparatus 11.

When the user performs the second-stage depression operation on the irradiation switch 23, the X-ray generation controller 21 transmits an X-ray irradiation signal for providing an instruction for X-ray irradiation, to the high-voltage generator 24 and the radiography control apparatus 11. Then, the high-voltage generator 24 applies high voltage to the X-ray tube assembly 25, and X-ray irradiation is started. It should be noted that the second-stage depression operation may be performed on the irradiation switch 23 before the start signal and the OK signal are received from the X-ray generation controller 21 and the FPD 12, respectively. In this case, upon receipt of the start signal and the OK signal, the X-ray irradiation signal is transmitted from the X-ray generation controller 21.

In the case where irradiation time has been set as in the case of plain radiography, X-ray irradiation is terminated when the predetermined irradiation time has elapsed. In the case of roentgenkymography, X-ray irradiation is continuously performed during a period of time in which the second-stage depression operation is performed on the irradiation switch 23, and when the irradiation switch 23 is released from the depression operation, the X-ray irradiation is terminated. Upon termination of the X-ray irradiation, the X-ray irradiation signal is turned off, and the OK signal, the start signal, and the ready signal are also sequentially turned off.

The X-ray image taken is transmitted from the FPD 12 to the radiography control apparatus 11, and stored in the storage 112. The X-ray image data are subjected to various image processing such as offset correction and gain correction in the radiography control apparatus 11, and are displayed on the display 113 (display controller 111A).

As described above, in the initial examination, irradiation conditions corresponding to radiography details included in an examination order are read from the storage 112, and are set in the X-ray generation controller 21 upon an instruction for executing the examination order. Irradiation conditions stored in the storage 112 are suitable for the case of examining an examination object with standard proportions.

In the case where a plurality of examination orders is registered for the same examination object, every time an instruction for executing an examination order is provided, radiography conditions (irradiation conditions) corresponding to radiography details included in the examination order are set in the X-ray generation controller 21, upon the instruction for executing the examination order. When an examination object is overweight or underweight, a user needs to make fine adjustments to irradiation conditions according to the body type of the examination object every time an instruction for executing an examination order is provided. That is, in the case where upon an instruction for executing an examination order, irradiation conditions are set as in the conventional manner, arithmetic processing and communication processing are wastefully performed.

Figure 3:
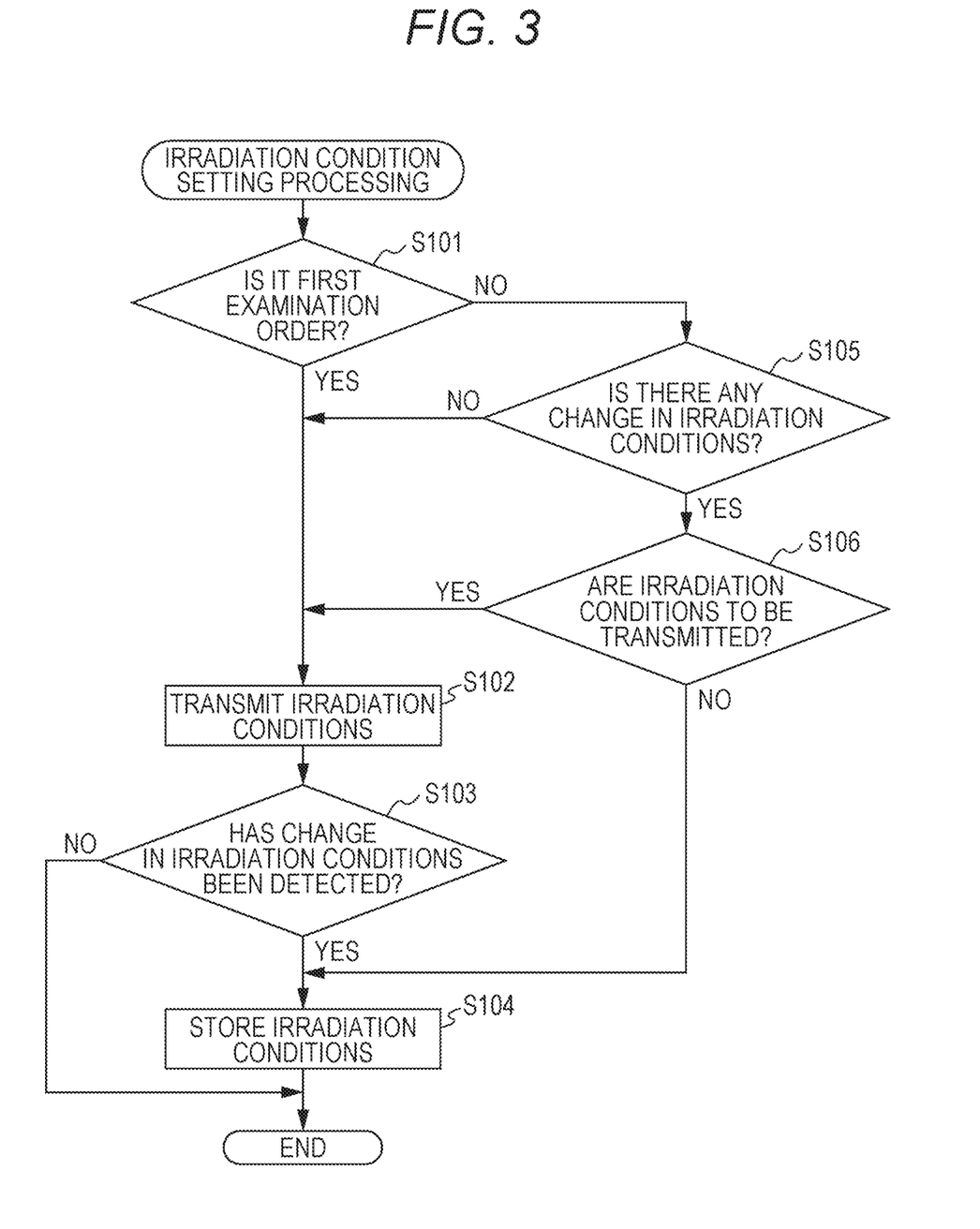
FIG. 3 is a flowchart showing an example of irradiation condition setting processing in the radiography control apparatus.

In the present embodiment, it is possible to efficiently reduce an operation burden on a user by setting irradiation conditions in the X-ray generator 20 according to the flowchart shown in FIG. 3.

FIG. 3 is a flowchart showing an example of irradiation condition setting processing in the radiography control apparatus 11. The processing is implemented by the CPU executing an irradiation condition setting program stored in the storage 112, as an instruction for executing an examination order is provided in radiography to be performed by the X-ray photography system 1.

In step S101, the processor 111 determines whether an examination order to be executed as per an instruction is the first examination order among a plurality of examination orders to be consecutively executed for the same examination object (operation as the transmission controller 111F). When it is the first examination order ("YES" in step S101), the process proceeds to step S102. When it is not the first examination order, that is, when it is the second or subsequent examination order ("NO" in step S101), the process proceeds to step S105. It should be noted that even in the case where just a single examination order is registered, if an X-ray is retaken due to an error in taking X-rays, an examination order for retaking an X-ray will be treated as the second or subsequent examination order.

In step S102, the processor 111 transmits irradiation conditions corresponding to radiography details of the examination order to the X-ray generator 20 (operation as the irradiation condition transmitter 111E). In other words, in the case of the first examination order, irradiation conditions are unconditionally transmitted from the radiography control apparatus 11 to the X-ray generator 20, and are set therein. It should be noted that in the initial examination, irradiation conditions read from the storage 112 are transmitted. In the second or subsequent examination, irradiation conditions of the previous examination registered as an examination history in the patient information included in an examination order are transmitted.

In step S103, the processor 111 determines whether the set irradiation conditions have been changed (operation as the transmission controller 111F). For example, when a change operation is performed through the X-ray generation console 22 in the X-ray generator 20, a signal indicating a change operation is transmitted to the radiography control apparatus 11. It is thus possible to determine whether irradiation conditions have been changed. When the irradiation conditions have been changed ("YES" in step S103), the process proceeds to step S104. When the irradiation conditions have not been changed ("NO" in step S103), the irradiation condition setting processing is terminated.

Hereinafter, an examination order with irradiation conditions changed is referred to as a "first examination order," and an examination order to be executed after the first examination order is referred to as a "second examination order." In some cases, an examination order for retaking an X-ray due to an error in taking X-rays may be treated as a second examination order.

In step S104, the processor 111 registers the changed irradiation conditions as the examination history in the patient information of the examination object (operation as the transmission controller 111F). In the next examination based on the same radiography details, there exist the irradiation conditions registered as a change history. As a result, in the next examination, the fine-tuned irradiation conditions will be set in the X-ray generator 20. It is thus possible to reduce an operation burden on a user.

In step S105, the processor 111 determines whether the irradiation conditions have been changed in the executed examination order, that is, whether an examination order to be executed as per an instruction is a second examination order (operation as the transmission controller 111F). For example, it is possible to determine whether the irradiation conditions have been changed in the executed examination order, by setting a flag indicating a condition change when a signal indicating a change operation is received. When the examination order is a second examination order ("YES" in step S105), the process proceeds to step S106. When the examination order is not a second examination order ("NO" in step S105), the process proceeds to step S102.

In step S106, the processor 111 determines whether to transmit irradiation conditions corresponding to the examination order (second examination order) (operation as the transmission controller 111F). When the irradiation conditions are to be transmitted ("YES" in step S106), the process proceeds to step S102. When the irradiation conditions are not to be transmitted ("NO" in step S106), the process proceeds to step S104.

Here, whether to transmit the irradiation conditions of a second examination order may be determined according to transmission settings made in advance. Alternatively, whether to transmit the irradiation conditions of a second examination order may be chosen in accordance with a user operation through the operator 114 for each instruction for executing the second examination order.

When the irradiation conditions are not transmitted, irradiation conditions will be set by the user through the X-ray generation console 22 (the irradiation conditions will be changed). These irradiation conditions are also registered as the examination history in step S104. It should be noted that when transmission of irradiation conditions is to be restricted, it is preferable to set whether to perform transmission for each parameter constituting the irradiation conditions. For example, among irradiation conditions, only set values of changed parameters are not allowed to be transmitted, and set values of other parameters are allowed to be transmitted. As a result, it is possible to reduce an operation burden on a user in setting irradiation conditions.

Figure 5:
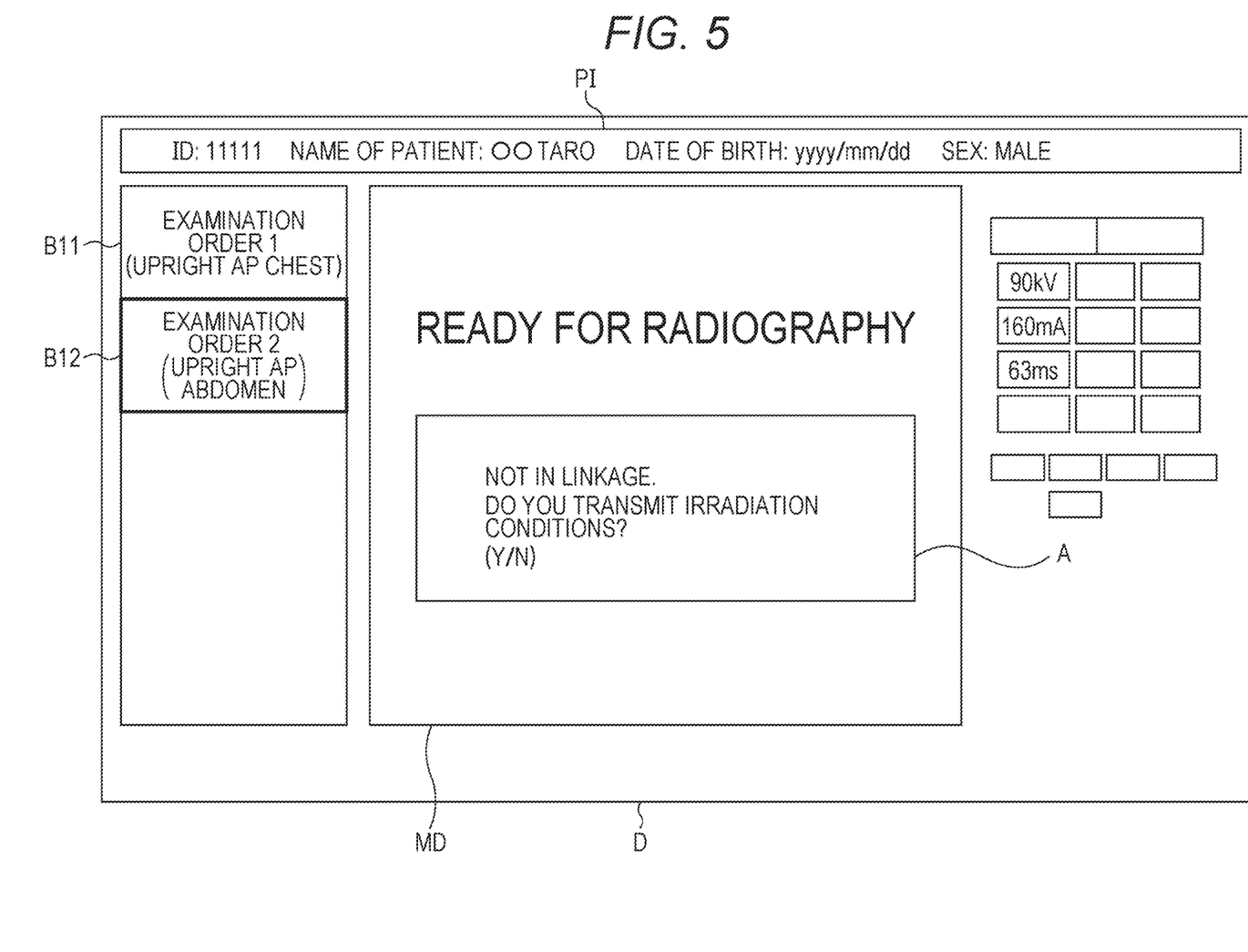
FIG. 5 is a diagram showing an example of the display screen at the time of providing an instruction for executing an examination order.

Moreover, when irradiation conditions are not transmitted, it is preferable to provide a representation of restrictions on transmission of the irradiation conditions corresponding to the examination order (see FIG. 5). As a result, the user can understand that irradiation conditions need to be set. It is thus possible to prevent radiography from being performed under erroneous irradiation conditions corresponding to the previous examination order.

Figure 4:
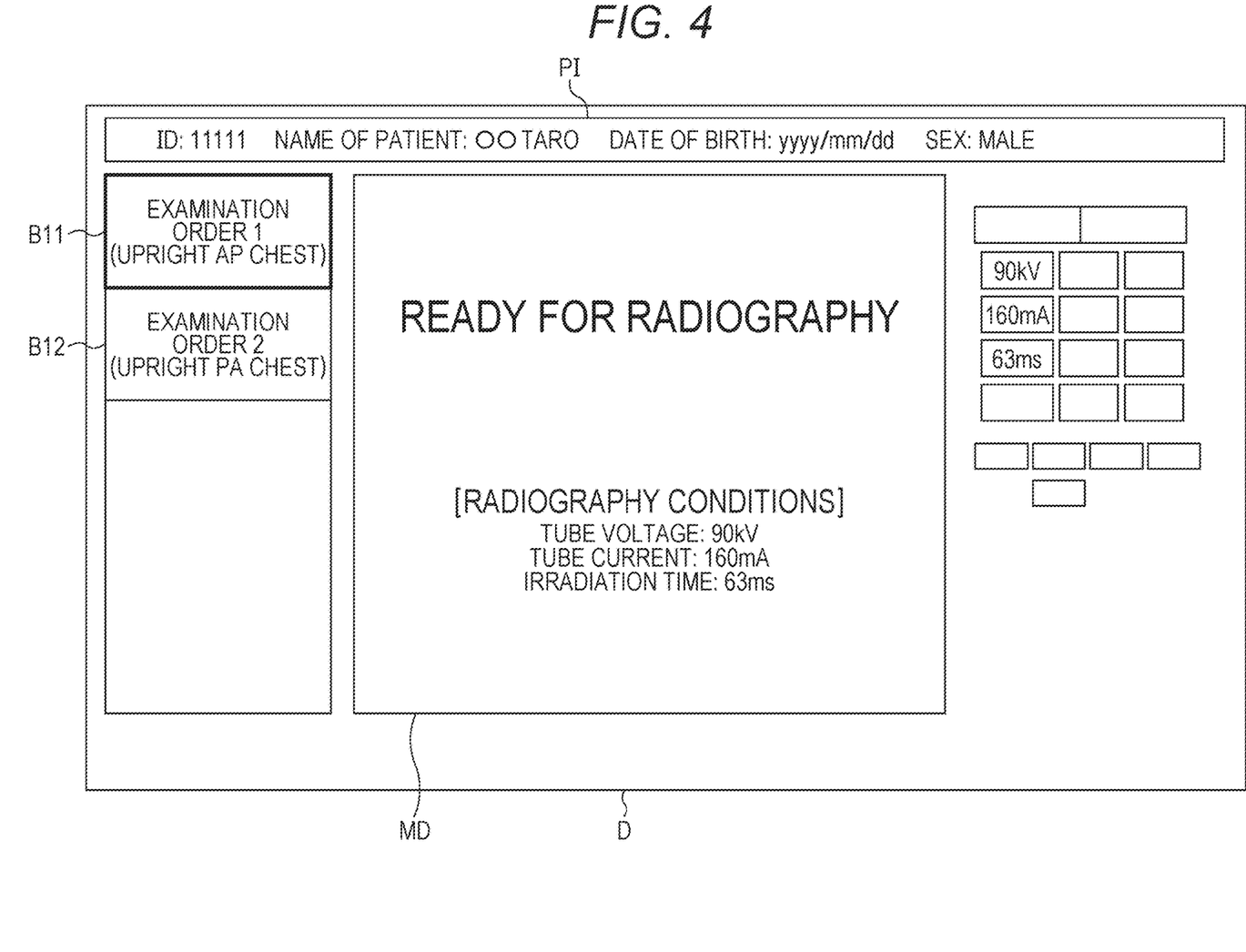
FIG. 4 is a diagram showing an example of a display screen at the time of providing an instruction for executing an examination order.

FIG. 4 and FIG. 5 are diagrams showing examples of a display screen D at the time of providing an instruction for executing an examination order. In FIG. 4 and FIG. 5, patient information PI is displayed on the upper part of the display screen D, and setting keys B11 and B12 for providing an instruction for executing an examination order are displayed on the left part of the display screen D. Additionally, radiography conditions and the like corresponding to a selected examination order are displayed in a main screen MD at the center of a setting screen.

The setting key B11 shown in FIG. 4 and FIG. 5 is selected in the case of providing an instruction for executing an examination order 1 of an upright AP chest radiograph (an X-ray taken from the front of an examination object in the upright position). The setting key B12 is selected in the case of providing an instruction for executing an examination order 2 of an upright AP abdomen radiograph. FIG. 4 shows a case in which the setting key B11 has been selected by a user to provide an instruction for executing the examination order 1. FIG. 5 shows a case in which the setting key B12 has been selected by a user to provide an instruction for executing the examination order 2. In the case where settings of irradiation conditions have been changed in execution of the examination order 1, an alarm display A is provided to indicate that transmission of irradiation conditions of the examination order 2 is restricted, as shown in FIG. 5.

As described above, the radiography control apparatus 11 (radiography supporter) according to the present embodiment supports the X-ray photography system 1 (radiography system) in taking radiographic images. The X-ray photography system 1 includes the X-ray generator 20 (radiation generator) and the X-ray photography apparatus 10 (radiography apparatus). The radiography control apparatus 11 includes the examination order acquirer 111D, the irradiation condition transmitter 111E, and the transmission controller 111F. The examination order acquirer 111D acquires an examination order. The irradiation condition transmitter 111E transmits corresponding X-ray irradiation conditions to the X-ray generator 20, for each examination order. In the case where a plurality of examination orders has been acquired for the same examination object, and irradiation conditions corresponding to a specific first examination order have been changed, the transmission controller 111F restricts transmission of irradiation conditions corresponding to a second examination order to be executed after the first examination order.

A radiography support method according to the present embodiment is a method of supporting the X-ray photography system 1 (radiography system) including the X-ray generator 20 (radiation generator) and the X-ray photography apparatus 10 (radiography apparatus) in taking radiographic images, the radiography support method including: a step of acquiring an examination order; a step of transmitting corresponding X-ray irradiation conditions to the X-ray generator 20, for each examination order; and a step of restricting transmission of irradiation conditions corresponding to a second examination order to be executed after a specific first examination order in a case where a plurality of the examination orders has been acquired for the same examination object, and the irradiation conditions corresponding to the first examination order have been changed.

According to the radiography control apparatus 11 (radiography supporter) and the radiography support method according to the embodiment, it is possible to efficiently reduce an operation burden on a user in setting irradiation conditions of the X-ray generator 20. In addition, when irradiation conditions are changed, irradiation conditions corresponding to the subsequent examination orders will not be transmitted to the X-ray generator 20, basically. Therefore, it is possible to prevent unnecessary arithmetic processing and communication processing from being performed, and reduce a processing burden on a computer accordingly.

Based on the embodiment, the invention made by the present inventors has been specifically described above. However, the present invention is not limited to the above-described embodiment, and changes may be made without departing from the scope of the invention.

For example, a case of applying the present invention to the X-ray photography system 1 of a stationary type to be installed in an X-ray room of a hospital has been described in the embodiment. Meanwhile, the present invention can also be applied to a mobile X-ray photography system to be installed in a visiting car.

In the embodiment, the present invention is implemented by the processor 111 (computer) functioning as the display controller 111A, the radiography condition setter 111B (irradiation condition transmitter 111E and transmission controller 111F), and the examination order acquirer 111D. Meanwhile, some or all of these functions can be implemented by an electronic circuit such as a digital signal processor (DSP), an application specific integrated circuit (ASIC), and a programmable logic device (PLD).

Furthermore, the present invention is not limited to an X-ray photography system, but can also be applied to a radiographing system using other radiation such as gamma rays.

Although embodiments of the present invention have been described and illustrated in detail, the disclosed embodiments are made for purposes of illustration and example only and not limitation. The scope of the present invention should be interpreted by terms of the appended claims rather than the foregoing description, and all changes which come within the meaning and range of equivalents of the claims are intended to be embraced therein.

What is claimed is:

1. A radiography supporter that supports a radiography system including a radiation generator and a radiography apparatus in taking radiographic images, the radiography supporter comprising
a hardware processor that:
acquires an examination order;
transmits corresponding radiation irradiation conditions to the radiation generator, for each examination order; and
restricts transmission of irradiation conditions corresponding to a second examination order to be executed after a specific first examination order in a case where a plurality of the examination orders has been acquired for a same examination object, and the irradiation conditions corresponding to the first examination order have been changed from the irradiation conditions corresponding to the first examination order to the irradiation conditions corresponding to the second examination order.

2. The radiography supporter according to claim 1, wherein
the irradiation conditions include a plurality of parameters, and
the hardware processor restricts transmission for each of the parameters.

3. The radiography supporter according to claim 1, wherein
the hardware processor restricts transmission of the irradiation conditions according to transmission settings made in advance.

4. The radiography supporter according to claim 1, wherein
the hardware processor is capable of setting whether to restrict transmission of the irradiation conditions for each second examination order.

5. The radiography supporter according to claim 1, wherein
the hardware processor shows that transmission of the irradiation conditions corresponding to the second examination order is restricted.

6. The radiography supporter according to claim 1, wherein
the second examination order includes an examination order for retaking a radiographic image due to an error in taking radiographic images.

7. The radiography supporter according to claim 1, wherein
the changed irradiation conditions are registered as an examination history of the examination object.

8. A radiography support method of supporting a radiography system including a radiation generator and a radiography apparatus in taking radiographic images, the radiography support method comprising:
acquiring an examination order;
transmitting corresponding radiation irradiation conditions to the radiation generator, for each examination order; and
restricting transmission of irradiation conditions corresponding to a second examination order to be executed after a specific first examination order in a case where a plurality of the examination orders has been acquired for a same examination object, and the irradiation conditions corresponding to the first examination order have been changed from the irradiation conditions corresponding to the first examination order to the irradiation conditions corresponding to the second examination order.

* * * * *